United States Patent
Hesse et al.

(10) Patent No.: US 11,793,828 B2
(45) Date of Patent: Oct. 24, 2023

(54) MICRORNA 19A/19B FOR USE IN TREATING A PATHOLOGICAL CONDITION ASSOCIATED WITH BONE LOSS OR REDUCED MUSCLE FUNCTION

(71) Applicant: UNIVERSITÄTSKLINIKUM HAMBURG-EPPENDORF, Hamburg (DE)

(72) Inventors: Eric Hesse, Hamburg (DE); Hanna Taipaleenmäki, Hamburg (DE); Hiroaki Saito, Puchheim (DE)

(73) Assignee: UNIVERSITÄTSKLINIKUM HAMBURG-EPPENDORF, Hamburg (DE)

( * ) Notice: Subject to any disclaimer, the term of this patent is extended or adjusted under 35 U.S.C. 154(b) by 0 days.

(21) Appl. No.: 17/320,649

(22) Filed: May 14, 2021

(65) Prior Publication Data

US 2021/0268014 A1  Sep. 2, 2021

Related U.S. Application Data

(63) Continuation of application No. 16/499,520, filed as application No. PCT/EP2018/058828 on Apr. 6, 2018, now Pat. No. 11,013,755.

(30) Foreign Application Priority Data

Apr. 6, 2017 (LU) ........................................ 100182

(51) Int. Cl.
| | | |
|---|---|---|
| C12N 15/11 | (2006.01) | |
| A61K 31/711 | (2006.01) | |
| A61P 19/10 | (2006.01) | |
| A61K 38/29 | (2006.01) | |

(52) U.S. Cl.
CPC ............ *A61K 31/711* (2013.01); *A61K 38/29* (2013.01); *A61P 19/10* (2018.01); *C12Q 2525/207* (2013.01); *C12Q 2600/178* (2013.01)

(58) Field of Classification Search
CPC ................................................ C12Q 2600/178
See application file for complete search history.

(56) References Cited

U.S. PATENT DOCUMENTS

2014/0219964 A1   8/2014   Wang et al.

FOREIGN PATENT DOCUMENTS

| RU | 2166940 | 5/2001 |
| WO | 2010071826 | 6/2010 |
| WO | 2017053622 | 3/2017 |

OTHER PUBLICATIONS

Xuan et al, Pluripotent stem cell-induced skeletal muscle progenitor cells with givinostat promote myoangiogenesis and restore dystrophin in injured Duchenne dystrophic muscle, Stem Cell Research & Therapy, 2021, 12:131, pp. 1-15 (Year: 2021).*
Xiu et al, Identification of hub genes, miRNAs and regulatory factors relevant for Duchenne muscular dystrophy by bioinformatics analysis, International Journal of Neuroscience, 2022, 132:3, 296-305 (Year: 2022).*
Rivas et al, miR-19b-3p is associated with a diametric response to resistance exercise in older adults and regulates skeletal muscle anabolism via PTEN inhibition, Am J Physiol Cell Physiol, 2021, 321: C977-C991 (Year: 2021).*
International Search Report and Written Opinion in corresponding PCT/EP2018/058828, dated Jul. 12, 2018.
Mogilyansky, et al., "The miR-17/92 cluster: a comprehensive update on its genomics, genetics, functions and increasingly important and numerous roles in health and disease", Cell Death and Differentiation (2013) 20, 1603-1614.
Tang, et al., "The role of MicroRNAs in Osteoclasts and Osteoporosis", RNA Biology, Feb. 18, 2015, 11:11, 1355-1363.
Coffey, et al., "MicroRNAs are central to osteogenesis: a review with a focus on cardiovascular calcification", Micro RNA Diagn. Ther. 2014; 1: 113-125.
Linh, et al., "The Role of MicroRNAs in Osteoarthritis and Chondrogenesis", Arthritis & Rheumatism, vol. 65, No. 8, Aug. 2013, pp. 1963-1974.
Gennari, et al., "MicroRNAs in bone diseases", Osteoporos Int (2017) 28:1191-1213.
Kocijan, et al., "Circulating microRNA Signatures in Patients With Idiopathic and Postmenopausal Osteoporosis and Fragility Fractures", J Clin Endocrinol Metab, Nov. 2016, 101(11):4125-4134.
Zhang, et al., "MicroRNA-19 (miR-19) Regulates Tissue Factor Expression in Breast Cancer Cells", J. Biological Chemistry, vol. 286, No. 2, pp. 1429-1435, Jan. 14, 2011.
Cheng, et al., "Antisense inhibition of human miRNAs and indications for an involvement of miRNA in cell growth and apoptosis", Nucleic Acids Research, 2005, vol. 33, No. 4.
Stenvang, et al., "Inhibition of microRNA function by antimiR oligonucleotides", Silence 2012, 3:1.

(Continued)

*Primary Examiner* — Ekaterina Poliakova-Georgantas
(74) *Attorney, Agent, or Firm* — Hovey Williams LLP

(57) ABSTRACT

The invention relates to inhibitors of microRNAs 19a and 19b and their use for treating or preventing conditions or diseases which are associated with bone loss, in particular osteoporosis and osteogenesis imperfect (OI). The inhibitors are also useful for inducing an anabolic effect in bone, either alone or when administered in combination with parathyroid hormone or a recombinant fragment thereof. The invention further relates to inhibitors of microRNAs 19a and 19b and their use for treating or preventing conditions or diseases which are associated with reduced muscle function, in particular muscle degeneration and muscle atrophy. The inhibitors are also useful for stabilizing and/or strengthening muscle function. In addition, inhibitors of microRNAs 19a and 19b can be used for treating or preventing cancer-related bone destruction or bone metastasis.

7 Claims, 6 Drawing Sheets

Specification includes a Sequence Listing.

(56) References Cited

OTHER PUBLICATIONS

Whitfield, et al., "The Bone-Building Action of the Parathyroid Hormone, Implications for the Treatment of Osteoporosis", Drugs & Aging Aug. 1999; 15 (2): 117-129.
Rauch, et al., "Osteogenesis imperfecta", The Lancet, vol. 363, Apr. 24, 2004.
Janssen, et al., "Treatment of HCV Infection by Targeting MicroRNA", N Engl J Med 2013;368:1685-94.
Musilova, et al., "MicroRNAs in B-cell lymphomas: how a complex biology gets more complex", Leukemia (2015) 29, 1004-1017.
Nielsen, et al., "High levels of microRNA-21 in the stroma of colorectal cancers predict short disease-free survival in stage II colon cancer patients", Clin Exp Metastasis (2011) 28:27-38.
Romao, et al., "MicroRNA regulation in mammalian adipogenesis", Experimental Biology and Medicine, 2011; 236; 9997-1004.
Hommers, et al., "Heterogeneity and Individuality: microRNAs in Mental Disorders", J Neural Transm (2015) 122:79-97.
Parfitt, et al., "Bone Histomorphometry: Standardization of Nomenclature, Symbols, and Units", J. Bone and Mineral Research, vol. 2, No. 6, 1987, 595-610.
Office Action in corresponding U.S. Appl. No. 16/499,520, dated Jul. 20, 2020.
Office Action in corresponding U.S. Appl. No. 16/499,520, dated Jan. 12, 2021.
Sievers, et al., "Altered microRNA expression in B lymphocytes in multiple sclerosis", Clinical Immunology, 2012, 144, pp. 70-79.
Office Action in corresponding Russian Patent Application Serial No. 2019135323/10, dated Jul. 12, 2021.
Palomo, et al., "Osteogenesis imperfecta: diagnosis and treatment", Curr Opin Endocrinol Diabetes Obes, 2017, 6, pp. 381-388.
Ralston, et al., "Management of Osteogenesis Imperfecta. Front Endocrinol (Lausanne)", 2020, 10(924), 10 pages.
Orwoll, et al., "Evaluation of teriparatide treatment in adults with osteogenesis imperfecta", J Clin Invest, 2014, 124(2), pp. 491-498.
Glorieux, et al., "BPS804 Anti-Sclerostin Antibody in Adults With Moderate Osteogenesis Imperfecta: Results of a Randomized Phase 2a Trial", Bone Miner Res, 2017, 32(7), pp. 1496-1504.
Sato, et al., "Glucocorticoid excess in Bone and muscle", Clin Rev Bone Miner Metab, 2018, 16(1), pp. 33-47.
Sato, et al., "Glucocorticoids induce Bone and muscle atrophy by tissue-specific mechanisms upstream of E3 ubiquitin ligases", Endocrinology, 2017, 158(3), pp. 664-677.
Kalyani, et al., "Age-related and disease-related muscle loss: the effect of diabetes, obesity, and other diseases", Lancet Diabetes Endocrinol, 2014, 2(10), pp. 819-829.
Yin, et al., "Over expressing miR-19b-1 suppress breast cancergrowth by inhibiting tumor microenvironmentinduced angiogenesis", Int J Biochem Cell Biol, 2018, 97, pp. 43-51 (abstract attached).

* cited by examiner a b

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: mRNA 19a-inhibitor

<400> SEQUENCE: 1
tgcatagatt tgcac                                                    15

<210> SEQ ID NO 2
<211> LENGTH: 15
<212> TYPE: DNA
<213> ORGANISM: Artificial Sequence
<220> FEATURE:
<223> OTHER INFORMATION: mRNA 19b inhibitor

<400> SEQUENCE: 2
tgcatggatt tgcac                                                    15

<210> SEQ ID NO 3
<211> LENGTH: 23
<212> TYPE: RNA
<213> ORGANISM: Homo sapiens

<400> SEQUENCE: 3
ugugcaaauc uaugcaaaac uga                                           23

<210> SEQ ID NO 4
<211> LENGTH: 23
<212> TYPE: RNA
<213> ORGANISM: Homo sapiens

<400> SEQUENCE: 4
ugugcaaauc caugcaaaac uga                                           23
```

MICRORNA 19A/19B FOR USE IN TREATING A PATHOLOGICAL CONDITION ASSOCIATED WITH BONE LOSS OR REDUCED MUSCLE FUNCTION

RELATED APPLICATIONS

This application is a continuation of U.S. Ser. No. 16/499,520, filed Sep. 30, 2019 as the U.S. National Stage of International Patent Application No. PCT/EP2018/058828, filed Apr. 6, 2018, which are each hereby incorporated by reference in its entirety, and which claim priority to Luxembourg Patent Application No. LU100182, filed Apr. 6, 2017.

SEQUENCE LISTING

The sequences listed in the accompanying Sequence Listing are presented in accordance with 37 C.F.R. 1.822. The "Sequence Listing" created on Apr. 13, 2021, is submitted as an ASCII computer readable text file, as 1 KB which is incorporated by reference herein.

FIELD OF THE INVENTION

Osteoporosis is the most prevalent disease of the musculoskeletal system in women and men, frequently leading to fragility fractures. These fractures often increase morbidity and mortality especially in the elderly and therefore represent a great medical and socio-economic burden. While bone is a highly dynamic tissue constantly dismantled and rebuilt throughout life by bone-resorbing osteoclasts and bone-forming osteoblasts, these processes are tightly coupled and balanced to keep the bone mass constant. With increasing age, bone resorption increases while bone formation decreases, leading to a reduction of bone mass and ultimately to osteoporosis.

Established anti-resorptive drugs like bisphosphonates or a RANKL-neutralizing antibody (Denosumab©) provide therapeutic approaches to osteoporosis by inhibiting osteoclast activity, thereby preventing further loss of bone mass. In contrast, the administration of a recombinant fragment of the parathyroid hormone (referred to as PTH 1-34 or teriparatide (Forteo©/Forsteo©) in the literature) is presently the only osteoanabolic therapy available. However, PTH therapy requires daily injections of the PTH 1-34 fragment, and the therapy is restricted to an overall time period of 24 months due to safety concerns. Accordingly, there is a need for additional therapies that prevent bone loss and/or result in an increase of bone mass and bone density.

MicroRNAs (miRNAs) are non-coding RNAs that can block the expression of protein-coding genes. miRNAs have been found to be encoded in the genome of numerous organisms, including mammalian and non-mammalian animals. miRNAs are capable of binding to the 3' untranslated region (3'-UTR) of the mRNA of a target gene owing to their base complementarity. Depending on the complementarity of the binding sequence and the proteins involved, miRNAs inhibit the translation of mRNA or induce the decomposition of the mRNA. Partial base complementarity between the miRNA and the cognate mRNA normally results in inhibition of mRNA translation, while perfect base complementarity induces mRNA degradation.

miRNAs are usually 18-24 nucleotides long and are produced by stepwise processing of precursor molecules. miRNAs are transcribed by polymerase II or III either from encoding genes or introns. The primary transcript resulting from the transcription of the genes is referred to as primary microRNA (pri-miRNA). It has a length of 500-3000 nucleotides and carries a 7-methylguanosine cap at the 5' end and a poly-A-tail at the 3' end. The pri-miRNA is processed by the RNAse III enzyme Drosha and the dsRNA binding protein DGCR8 in the nucleus of the cell to a precursor microRNA (pre-miRNA) of 70-80 nucleotides in length. The pre-miRNA forms a characteristic hairpin structure and is exported through the nucleic pores to the cytoplasma where it is processed by the RNAse III enzyme Dicer into ds-miRNAs of a length between 17-24 nucleotides. Dicer interacts with a protein that specifically binds to the ds-miRNAs to unwind these duplexes. The resulting ss-miRNAs can interfere with the expression of the respective target mRNA.

Several miRNAs have been reported to be involved in the regulation of numerous physiological and developmental processes. Recently, miRNAs have gained considerable attention as potential therapeutic targets for treating diseases like hepatitis C [1], chronic lymphocytic leukemia [2], colorectal cancer [3], obesity [4], or schizophrenia [5].

The present invention is based on the insight that miRNA-19a and miRNA-19b are involved in the regulation of bone-formation and that inhibition of these miRNAs is a highly efficient way to prevent or reduce bone loss. Accordingly, the inhibition of these miRNAs is useful for treating diseases like osteoporosis which are associated with a loss of bone mass. The inhibitors of miRNA-19a and miRNA-19b exert an anabolic effect and can be used alone or in combination with each other. In a preferred embodiment, one or more inhibitors of miRNA-19a and/or miRNA-19b are used in combination with the parathyroid hormone or a fragment thereof, such as PTH 1-34, for an enhanced bone anabolic effect. The invention further shows that miRNA-19a and miRNA-19b are involved in the regulation of muscle regeneration, and in particular in the prevention of reduced muscle mass, strength and/or performance. As shown in the below Examples, inhibition of these miRNAs is effective in preventing a loss in muscle function under various conditions. Inhibition of these miRNAs is hence also useful for treating diseases like muscular dystrophy, muscle atrophy, sarcopenia, or cachexia, such as cancer-induced cachexia. The invention further shows that miRNA-19a and miRNA-19b inhibitors can be used for the prevention or treatment of cancer-induced bone destruction and bone metastasis, in particular breast cancer metastasis to bone.

SUMMARY OF THE INVENTION

In one aspect, the invention provides an inhibitor of microRNA 19a and/or microRNA 19b for use in a method of treating a disease that is associated with bone loss. A disease which is associated with a pathological degree of bone loss may be, for example, a disease that is characterized by an abnormal bone resorption and/or bone formation in conditions of high bone turnover. It is shown herein below that the inhibition of microRNA 19a and/or microRNA 19b results in a strong bone anabolic effect which demonstrates the usefulness of microRNA 19a and/or microRNA 19b inhibitors for treating diseases and conditions in which a pathological level of bone loss occurs. Such diseases and conditions include in particular osteoporosis and osteogenesis imperfect (CI). Thus, in a preferred aspect, the disease and condition to be treated by the microRNA 19a and/or microRNA 19b inhibitors is osteoporosis. As used herein, the term "osteoporosis" includes all forms of osteoporosis, such as primary, secondary and postmenopausal osteoporosis. Also included are sex steroid deficiency-induced osteoporosis and glucocorticoid-induced osteoporosis. The inhibitors will also be useful for treating conditions which require a bone anabolic effect. For example, temporary use of the inhibitors in patients with bone fractures can assist the natural healing process by the induction of bone mass. In a preferred aspect, the inhibitor of microRNA 19a and/or microRNA 19b is used alone, i.e. without any other active ingredient. In another preferred aspect, the inhibitor of microRNA 19a and/or microRNA 19b is used in combination with parathyroid hormone or a fragment thereof, such as PTH 1-34. The inhibitor of microRNA 19a and/or microRNA 19b effectively augments the bone anabolic effect conferred by PTH 1-34.

In another aspect, the invention provides an inhibitor of microRNA 19a and/or microRNA 19b for use in a method of treating a disease that is associated with a loss in muscle mass or function. It was found by the present inventors that inhibiting microRNA 19a and/or microRNA 19b expression significantly increases or restores muscle function. Hence, inhibitors of microRNA 19a and/or microRNA 19b are likewise suitable for therapeutic use in the treatment of diseases like muscular dystrophy or muscle atrophy. In a preferred aspect, the microRNA 19a and/or microRNA 19b inhibitors are used for treating muscular dystrophy, sarcopenia, cachexia, such as cancer-induced cachexia, or muscle atrophy. In another preferred aspect, the microRNA 19a and/or microRNA 19b inhibitors are used for treating a loss of muscle function that is associated with osteoporosis, such as sex-steroid deficiency-induced or glucocorticoid-induced osteoporosis. In another preferred aspect, the microRNA 19a and/or microRNA 19b inhibitors are used for treating a loss of muscle function that is associated with breast cancer bone metastases. In yet another preferred aspect, the microRNA 19a and/or microRNA 19b inhibitors are used for treating a loss of muscle function that is associated with osteogenesis imperfecta (CI). In yet another preferred aspect, the microRNA 19a and/or microRNA 19b inhibitors are used for treating a loss of muscle function that is associated with a muscle dystrophy, in particular a hereditary muscle dystrophy due to a mutation of the dystrophin gene, e.g. type Duchenne or type Becker-Kiener.

In another aspect, the invention provides an inhibitor of microRNA 19a and/or microRNA 19b for use in a method of preventing or treating cancer-related bone destruction. It was found herein that inhibitors of microRNA 19a and/or microRNA 19b effectively inhibit the proliferation of bone destructive MDA-MB-231 metastatic breast cancer cells. Accordingly, inhibitors of microRNA 19a and/or microRNA 19b can be used for the therapeutic treatment or the prevention of cancer-related osteolysis, the treatment or prevention of bone metastasis, such as bone metastasis originating from breast cancer.

In a particular preferred embodiment, the invention provides an inhibitor of microRNA 19a and/or microRNA 19b for use in a method of treating osteogenesis imperfecta (CI). Osteogenesis imperfecta, also known as brittle bone disease, is a rare genetic disorder affecting the bones, which is caused by one or more mutations in the gene encoding collagen type I. Several mutations and subtypes have been identified that cause OI. People with OI may have broken bones with little or no trauma. OI can range from very severe to mild. Individuals with the most severe type of CI may die at birth. People with severe CI who survive may have bowed arms and legs, very short stature and be unable to walk. People with the mildest form of CI may only break bones occasionally and have normal height and lifespan. Breaks can occur in any bone, but are most common in the arms and legs. The current standard-of-care for severe types of CI involves the use of bisphosphonates and surgery to put rods in bones to strengthen them. An anti-resorptive treatment with bisphosphonates is directed to the reduction of osteoclast-dependent bone resorption. By reducing resorption, a higher bone mass is obtained.

Although the bone quality remains poor, a higher bone mass significantly reduces the fracture risk. In addition, bone-forming agents have been shown to be effective in further increasing the bone mass and are currently examined in clinical trials. Since inhibitors of microRNA 19a and/or microRNA 19b have been shown herein to improve bone formation and bone mass under various conditions, they will be suitable for the treatment of CI.

DETAILED DESCRIPTION OF THE INVENTION

It is known that microRNA 19a and/or 19b are expressed from the polycistronic cluster miR-17~92, which contains the miRNAs 17, 18, 19a, 20a, 19b-1, and 192. Some of these microRNAs have previously been associated with cancer in humans.

The invention proposes the use of inhibitors of microRNA 19a and/or 19b for treating diseases that are associated either with bone loss or reduced muscle function. While the invention is not limited in this respect, it is preferred that the subject afflicted with the diseases or condition is a human subject. Preferably, the subject will be at least 30 years old, preferably at least 40 years old, at least 45 years old, at least 50 years old, at least 55 years old, at least 60 years old, or at least 65 years old.

In principle, any type of molecule can be used which interferes with microRNA 19a and/or microRNA 19b or their pre-miRNA to reduce or block the expression or function of any of those microRNAs or their corresponding pre-miRNAs. It is preferred that the inhibitors used herein are nucleic acid molecules, such as ribonucleic acid (RNA) or deoxyribonucleic acid (DNA) molecules, or derivatives thereof which have been modified as explained below. It is particularly preferred that the inhibitors are DNA or RNA oligonucleotides comprising or consisting of a sequence that allows them to hybridize to their cognate miRNAs, i.e. microRNA 19a and/or microRNA 19b, to form a duplex that prevents binding of the microRNAs to their target mRNA. Other techniques for the inhibition of microRNA 19a and/or microRNA 19b or their pre-miRNA are known to the person of skill and include microRNA sponges, Lentivector-based anti-microRNAs (miRZip) and Tough Decoy inhibitors.

As used here, the term "oligonucleotide" refers to an oligomer or polymer of nucleotide monomers. According to the invention, the oligonucleotide can be of any length, but it will preferably have a length of 8 to 50 nucleotides, more preferably 10 to 40 nucleotides, 12 to 30 nucleotides, 15 to 25 nucleotides, and most preferably 18 to 24 nucleotides. For example, the oligonucleotide may have a length of 10, 12, 14, 16, 18, 20, 22, 24, 26, 28, 30, 32, 34, 36, 38, 40, 42, 44, 46, 48 or 50 nucleotides. For some applications, the oligonucleotide may also comprise more than 50 nucleotides, for example 60, 70, 80, 90 or 100 nucleotides. The oligonucleotide can be a single-stranded, double-stranded, or partially double stranded nucleic acid molecule. Methods for producing oligonucleotides are widely known and comprise chemical synthesis or PCR-based methods.

The oligonucleotide will preferably consist of nucleotide monomers that are joined together by phosphodiester bridges. It is, however, also possible to use oligomers or polymers in which the sugar-phosphate backbone has been replaced with functionally similar structures, for example with a peptide backbone or with a phosphoramide, thiophosphate, methylphosphonate or dithiophosphate backbone. In some cases, these modifications result in an increased resistance of the oligonucleotide against enzymatic decomposition by nucleases after administration into the subject to be treated.

Moreover, oligonucleotides that have one or more modified sugar residues are also covered by the invention. For example, one or more hydroxyl groups can be replaced with halogens or aliphatic groups, or they can be functionalized with ethers, amines or similar structures. In a preferred embodiment, the oligonucleotide comprises one or more sugars in which the 2' hydroxyl has been modified by adding a methyl (OMe) or a methoxy-ethyl (MOE) group. These sugar modifications provide for higher stability and resistance against enzymatic decomposition.

The oligonucleotide of the invention may also comprise modified bases, alongside or instead of the naturally occurring bases adenine, guanine, thymine, cytosine and uracil. Said modified bases comprise, for example, 5-methylcytosine, 5-hydroxymethylcytosine, xanthine, hypoxanthine, 2-aminoadenine, 6-methyladenine, 6-methylguanine, 2-thiouracil, 2-thiothymine, 2-thiocytosine, 5-halouracil, 5-halocytosine, 5-propinyluracil, 5-propinylcytosine, 6-azouracil, 6-azocytosine, 6-azothymine, 5-uracil, 4-thiouracil, 8-thioalkyladenine, 8-hydroxyladenines, 8-thioladenine, thioalkylguanine, 8-hydroxylguanine, 8-thiolguanine, 7-methylguanine, 7-methyladenine, 8-azaguanine and 8-azaadenine, 7-deazaguanine, 7-deazaadenine, 3-deazaguanine and/or 3-deazaadenine.

Apart from the above, the oligonucleotide of the invention may also comprise one or more modifications at its 3' and/or 5' terminus. For example, one or both of the termini can be linked to protection groups to make the oligonucleotide less susceptible to enzymatic decomposition by nucleases.

Preferably, the inhibitors of microRNA 19a and/or microRNA 19b are substantially complementary to microRNA 19a and/or microRNA 19b. The sequence of the inhibitors anti-microRNA 19a (5'-TGCATAGATTTGCAC-3') and anti-microRNA 19b (5'-TGCATGGATTTGCAC-3') are set out in SEQ ID NO:1 and SEQ ID NO:2, respectively. The sequence of to microRNA 19a and microRNA 19b set out in SEQ ID NO:3 and SEQ ID NO:4, respectively. An oligonucleotide is substantially complementary to any of these sequences if it comprises at least 70% sequence identity over a stretch of at least 10, 12, 14, 16, 18 or 20 nucleotides. Preferably, the oligonucleotide has at least 70% sequence identity over a stretch of 20 nucleotides. Preferably, the sequence identity is at least 80%, at least 90%, or at least 95%. It is particularly preferred that the oligonucleotide is completely complementary over a stretch of at least 10, 12, 14, 16, 18 or 20 nucleotides. In one embodiment, the region of complementarity will have less than 5 mismatches, e.g. 4, 3, 2, or 1 mismatch.

In a particularly preferred aspect, the inhibitor of microRNA 19a and/or microRNA is a DNA comprising
(a) the sequence of SEQ ID NO:1 or SEQ ID NO:2, or
(b) the complement of the sequence of SEQ ID NO:1 or SEQ ID NO:2, or
(c) a variant of any of the sequences of (a) or (b) which has at least 70% sequence identity thereto and is capable of hybridizing to microRNA 19a and/or microRNA 19b.

The inhibitors disclosed above are preferably administered as a pharmaceutical composition. Thus, in another aspect, the present invention provides pharmaceutical compositions comprising an (a) inhibitor of microRNA 19a and/or microRNA 19b, such as a nucleic acid or a nucleic acid analog, and (b) a pharmaceutically acceptable carrier. As described above, the inhibitor will preferably be a DNA or RNA molecule. In one aspect, the pharmaceutical composition is preferably for use in a method of treating a disease that is associated with bone loss. In another aspect, the pharmaceutical composition is preferably for use in a method of treating a disease that is associated with a loss of muscle function.

The preparation of pharmaceutical compositions comprising nucleic acid-based inhibitors is well known by those working in the field of pharmaceutics. Typically, such compositions are prepared for injection either as liquid solutions or suspensions. The pharmaceutically active inhibitor can be mixed with excipients that are compatible with the inhibitors when used in human patients. The pharmaceutical compositions of the invention normally comprise a physiologically acceptable carrier together with the microRNA inhibitor molecules dissolved or dispersed therein as an active ingredient.

Pharmaceutically acceptable carriers comprise, for example, water, saline, Ringer's Solutions, or dextrose solution. Further suitable carriers for compositions comprising the microRNA inhibitors are described in standard textbooks, for example, in "Remington's Pharmaceutical Sciences", Mack Pub. Co., New Jersey (1991). In addition to a carrier, the pharmaceutical composition of the invention may also comprise wetting agents, buffering agents, stabilizers, dyes, preservatives and the like in any concentration, provided that these compounds do not interfere with the inhibitory activity of the microRNA inhibitors of the invention.

Different routes of administration are feasible for providing the microRNA inhibitors to the site that requires treatment. The pharmaceutical composition may be formulated, e.g. for parenteral administration. Parenteral administration includes intravenous, intradermal, intraarterial, subcutaneous, topical, transmucosal, transdermal or rectal administration. According to a particularly preferred embodiment, the pharmaceutical composition is formulated for injection or infusion.

Pharmaceutical compositions suitable for injection normally include sterile aqueous solutions or dispersions and sterile powders for the extemporaneous preparation of sterile injectable solutions or dispersions. The composition should furthermore be stable under regular conditions of manufacturing and storage. For maintaining sterility, the pharmaceutical composition normally includes preservatives, such as parabens, chlorobutanol, phenol, ascorbic acid, thimerosal, and the like, to suppress microbial growth in the product. For intravenous or intraarterial administration, suitable carriers may comprise physiological saline, bacteriostatic water, Cremophor EL™ (BASF) or phosphate buffered saline (PBS). The carrier may also be a solvent or dispersion medium containing, for example, water, ethanol, polyol (for example, glycerol, propylene glycol, and liquid polyethylene glycol, and the like), and suitable mixtures thereof. A prolonged absorption of the injectable compositions can be achieved by including into the composition an agent which delays absorption, for example, aluminum monostearate or gelatin. Sterile injectable solutions can be prepared by incorporating the microRNA inhibitors in the required amount in an appropriate solvent with one or more of the above mentioned ingredients followed by sterile filtration. Similarly, dispersions are prepared by incorporating the microRNA inhibitors into a sterile vehicle that contains a dispersion medium and optionally other ingredients as outlined above. Sterile solutions can also be obtained by providing the microRNA inhibitors in the form of a sterile powder by methods known in the art, such as vacuum drying or freeze-drying, and reconstituting the powder with a sterile liquid to yield the final solution for injection. Alternatively, the pharmaceutical composition according to the invention may also be administered by continuous infusion.

Administration of the pharmaceutical composition may also be achieved by transmucosal or transdermal delivery. For transmucosal or transdermal administration, the pharmaceutical composition comprising the microRNA inhibitors of the invention will comprise penetrants which are appropriate for crossing the skin or mucosal barrier. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Transdermal compositions can be administered, for example, by patches or microneedles. Preferably, the compounds are prepared in the form of suppositories, with conventional suppository bases such as cocoa butter and other glycerides for rectal delivery.

In one embodiment, the microRNA inhibitors are prepared with carriers that will protect the inhibitors against elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparing controlled release formulations are well-known in the art. Furthermore, sustained-release compositions may be prepared. Suitable examples of sustained-release preparations include semipermeable matrices of solid hydrophobic polymers, which matrices are in the form of shaped articles, e.g., films or microcapsules. Examples of sustained-release matrices include polyesters, hydrogels, polylactides, co-polymers of L-glutamic acid and ethyl-L-glutamate, non-degradable ethylene-vinyl acetate, degradable lactic acid-glycolic acid copolymers and the like.

In a further aspect, the present invention provides a method of treating a disease or condition which is associated with a pathological level of bone loss, such as osteoporosis and CI, comprising the administration of a therapeutically effective amount of an inhibitor of microRNA 19a and/or microRNA 19b or a pharmaceutical composition as defined above comprising such inhibitor(s). In yet another aspect, the present invention provides a method of treating a disease or condition which is associated with a loss in muscle function, such as muscular dystrophy, sarcopenia, cachexia, such as cancer-induced cachexia, or muscle atrophy, comprising the administration of a therapeutically effective amount of an inhibitor of microRNA 19a and/or microRNA 19b or a pharmaceutical composition as defined above comprising such inhibitor(s).

A therapeutically effective amount of the microRNA inhibitors is typically an amount which—upon administration—is sufficient to effectively block or reduce the expression of microRNA 19a and/or microRNA 19b or their respective pri- or pre-miRNAs. In principle, any type of molecule can be used for the purpose of the invention which interferes with the expression of microRNA 19a and/or microRNA 19b.

It will be appreciated by those skilled in the art that the amount of the inhibitor which is to be administered to the patient will depend on several factors, such as age and weight of the patient, as well as the nature and severity of the symptoms to be treated. The amount of the inhibitor which exerts the desired therapeutic effect may be determined in each patient case by use of routine experimentation. Typically, the dosage of the microRNA inhibitor per body weight varies from about 0.1 mg per kg body weight of the patient to about 50 mg per kg body weight of the patient, and more preferably from about 0.5 mg per kg body weight of the patient to about 20 mg per kg body weight of the patient, and even more preferably from 1 mg per kg body weight of the patient to about 10 mg per kg body weight of the patient. The administration regimen may include one or more administrations of the inhibitor daily.

For example, the treatment may be continued for at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or at least 12 weeks. For some indications, the treatment may be continued for at least 4 months, at least 5 months, at least 6 months, at least 7 months, at least 8 months, at least 9 months, at least 10 months, at least 11 months, at least 12 months or at least 18 months. The treatment period will be determined by the medical practitioner in consideration of several factors, such as the nature and severity of the symptoms to be treated, the route of administration, and the like.

EXAMPLES

Example 1: In Vivo Analysis of miRNA Expression

To identify miRNAs that are regulated in response to a bone anabolic stimulus, we injected 8-week old mice with a recombinant fragment of human parathyroid hormone (PTH1-34) or an antibody against sclerostin (Scl-Ab). Specifically, wild type male mice were injected with vehicle, 100 μg/kg PTH1-34 (Bachem) or 100 μg/kg Scl-Ab. After 4 hours, total RNA including small RNAs was isolated from mouse bones using Trizol (Invitrogen) according to instructions provided by the manufacturer. For expression analysis, cDNA was synthesized from 1 μg of total RNA using ProtoScript First Strand cDNA Synthesis Kit (NEBioLabs). Quantitative real-time PCR (qRT-PCR) was performed with the CFX96 detection system (BioRad) using SYBR Green Master Mix (BioRad). After normalization to TATA-binding protein (Tbp) mRNA, relative expression levels and fold induction of each target gene were calculated using the comparative CT (ΔΔCT) method. Small RNAs were isolated from various mouse tissues with Trizol. The QuantimiR-kit (SBI System Biosciences) was used to add a polyA tail to the small RNAs for cDNA synthesis according to manufacturer's guidelines. Relative miRNA expression was determined by SYBR Green detection (BioRad) using a universal reverse primer and a specific forward primer designed for each miRNA of interest. U6 expression was used as internal control, and the relative miRNA expression was calculated using the ΔΔCT method.

Figure 1:
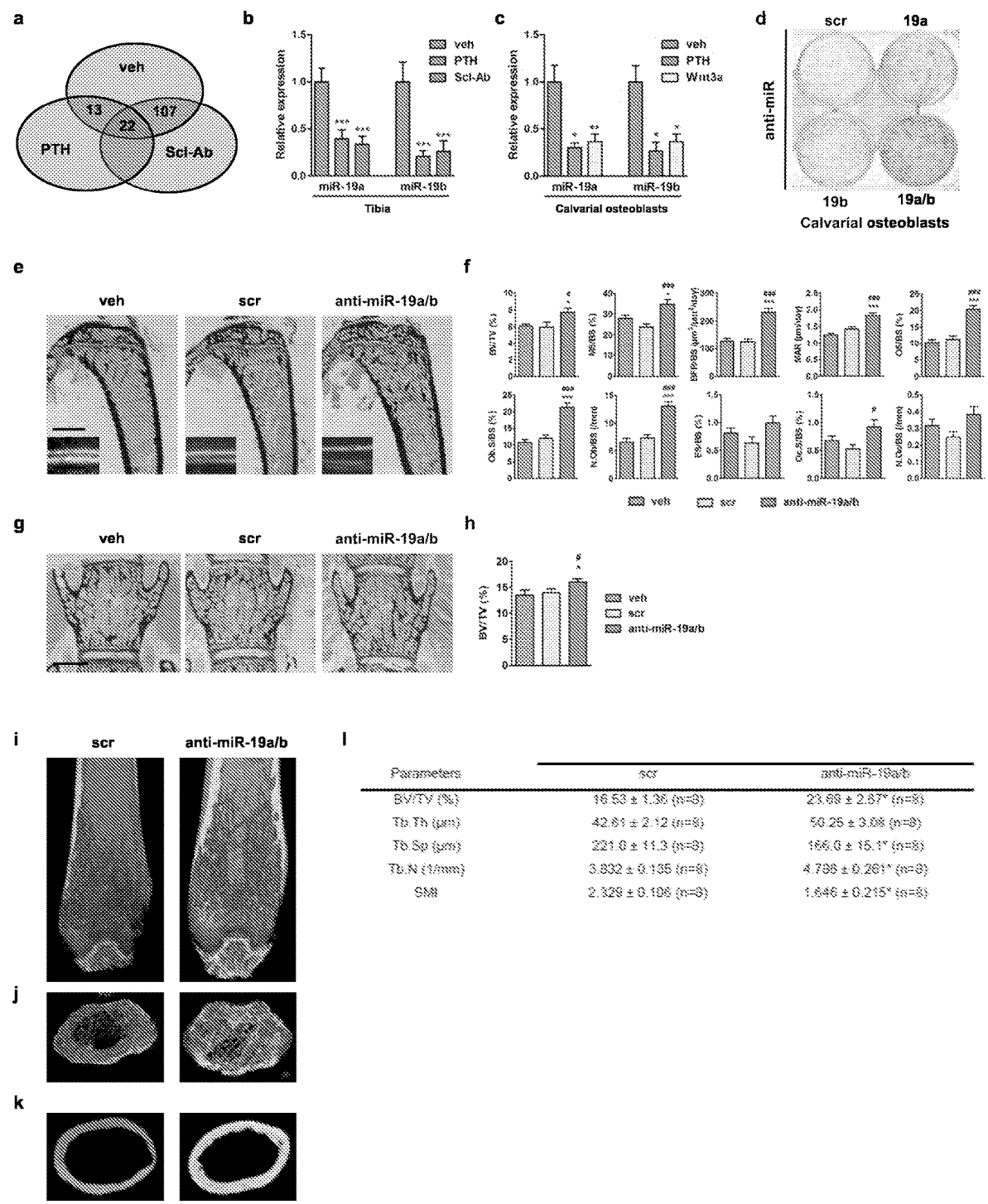
FIG. 1 shows the increase in bone mass in vivo by inhibition of miR-19a/b. (a): Venn diagram of miRNAs that were reduced by treatment of mice with PTH or an antibody against Sclerostin, respectively. (b): Expression of miR-19a and miR-19b in bones from mice treated with PTH or Scl-Ab. (c): Expression of miR-19a and miR-19b in calvarial osteoblasts stimulated in vitro with PTH or Wnt3a. (d): Differentiation of calvarial osteoblasts transfected with a scrambled control miRNA inhibitor (scr), inhibitors (anti-miR) of miR-19a or miR-19b or a combination of anti-miR-19a and -19b (19a/b) evaluated by staining of alkaline phosphatase activity. (e): Von Kossa staining of the proximal tibiae, and fluorescence double labelling of bone formation (insets). (f): Histomorphometric analysis of the proximal tibiae. (g): Von Kossa staining of the fourth lumbar vertebrae of the same animals as in (e)-(f). (h): BV/TV of the fourth lumbar vertebrae of the same animals as in (e)-(f). Mean values±SEM. * $p<0.05$,  $p<0.01$, * $p<0.001$ vs. vehicle, #$p<0.05$, ###$p<0.001$ vs. Scramble. (i)-(k): Micro-computed tomography (µCT) scans of the distal femura (i,j) and of midshaft femoral cross sections (k) of the same animals as in (e), after termination of the treatment. (l): Quantification of the µCT analysis of the distal femura of the same animals as in (e). Mean values±SEM. * $p<0.05$ vs. Scramble. Abbreviations: BV/TV, bone volume/tissue volume; MS/BS, mineralizing surface/bone surface; BFR/BS, bone formation rate/bone surface; MAR, mineral apposition rate; OS/BS, osteoid surface/bone surface; Ob.S/BS, osteoblast surface/bone surface; N.Ob/BS, number of osteoblasts/bone surface; ES/BS, eroded surface/bone surface; Oc.S/BS, osteoclast surface/bone surface; N.Oc/BS, number of osteoclasts/bone surface; Tb.Th, trabecular thickness; Tb.Sp, trabecular separation; Tb.N, trabecular number; SMI, structural modeling index.

Results: Challenging mice by PTH or Scl-Ab treatment reduced the expression of 35 or 129 miRNAs in bone, respectively. It was found that 22 miRNAs were downregulated by both treatments (FIG. 1a). Among the commonly down-regulated miRNAs, miR-19a and miR-19b were identified. Direct quantification of miR-19a/b expression in bone confirmed their negative regulation by PTH and Scl-Ab (FIG. 1b).

Example 2: In Vitro Analysis of miRNA Expression

For testing the effect of a stimulation of calvarial osteoblasts with PTH1-34 and Wnt3a, an in vitro assay was performed. Calvarial osteoblasts were isolated from 2-3-day old mice and expanded in α-MEM containing 10% FBS and P/S. Osteoblasts were stimulated with vehicle, PTH 1-34 (100 μM) or Wnt3a (100 ng/ml) for 4 hours and small RNAs were extracted from cells using the miRNEasy kit (Qiagen). After cDNA synthesis, expression of miR-19a and miR-19b was analyzed using qRT-PCR. U6 expression was used as internal control, and the relative miRNA expression was calculated using the ΔΔCT method.

Results: Both the stimulation with PTH1-34 and Wnt3a induced a reduction in miR-19a/b expression in calvarial osteoblasts (FIG. 1c).

Example 3: In Vitro Analysis of Osteoblast Differentiation

To test whether the differentiation of calvarial osteoblasts can be influenced by interfering with miR-19a/b expression, the cells were transfected with oligonucleotides that are designed to bind to and inhibit endogenous miR-19a (anti-miR-19a: 6-FAM/TGCATAGATTTGCAC) and miR-19b (anti-miR-19b: 6-FAM/TGCATGGATTTGCAC). These synthetic oligonucleotides contain phosphorothioate backbone bonds for optimal use in functional studies as well as optimized pharmacokinetic and pharmacodynamic properties and minimal toxicity. Furthermore, the 5' fluorescein FAM label allows monitoring of transfection efficiency in vitro and tissue delivery in vivo. The cells were transfected with anti-miR-19a/b (50 nM) using the Neon electroporation system (Invitrogen). Osteoblast differentiation was induced by supplementing α-MEM with 0.2 mM L-ascorbic acid and 10 mM β-glycerophosphate (both Millipore). Osteoblast differentiation was determined by alkaline phosphatase (ALP) staining after fixing the cells in 4% neutrally buffered formaldehyde solution. For ALP staining, cells were incubated with naphthol AS-MX/Fast Blue (both Sigma-Aldrich) in Tris-HCl solution for 15 min at room temperature.

Results: It was found that differentiation of calvarial osteoblasts was enhanced by transfection with inhibitors against miR-19a and miR-19b in a synergistic way (FIG. 1d).

Example 4: Bone Analyses in Mice Treated with Anti-miR-19a/b

To test whether the treatment with a combination of inhibitors against miR-19a and miR-19b (anti-miR-19a/b) might exert a bone anabolic effect in vivo, 8-week old mice were treated for 28 days by weekly intravenous (i.v.) injections of anti-miR-19a/b and subsequent determination the bone mass. Mice were injected 7 and 2 days before sacrifice with calcein (40 mg/kg) and democycline (20 mg/kg, Sigma-Aldrich), respectively. Tibiae and the fourth lumbar vertebral bodies (L4) were collected and fixed in 3.7% PBS-buffered formaldehyde. For histomorphometrical analysis, tibiae and L4 were embedded in methylmethacrylate, and Toluidine blue. Von Kossa and Tartrate-resistant acid phosphatase (TRAP) stainings were performed using 4 μm sagittal sections. Quantitative bone histomorphometric measurements were performed according to standardized protocols (ASBMR standards) [6] using an OsteoMeasure system (OsteoMetrics). Microcomputed tomography (μCT) was used for three dimensional analyses of long bone and vertebral body bone properties. The fourth lumbar vertebral bodies (L4) of mice were analyzed using high-resolution microcomputed tomography with a fixed isotropic voxel size of 10 μm (70 peak kV at X μA 400 ms integration time; Viva80 micro-CT; Scanco Medical AG). This threshold was verified by manually evaluating 10 single tomographic slices from four samples per group to isolate the mineralized tissue and to preserve its morphology while excluding nonmineralized tissues. All analyses were performed on the digitally extracted bone tissue using 3D distance techniques (Scanco Medical AG).

Results: The treatment with anti-miR-19a/b increased the trabecular bone mass of the proximal tibia. Histomorphometric analysis revealed that anti-miR-19a/b treatment activated bone remodeling by augmenting osteoblast and osteoclast parameters with an enhanced bone formation that led to a net increase in bone mass (FIGS. 1e and 1f). The bone anabolic effect of anti-miR-19a/b treatment was confirmed at L4 vertebral bodies (FIGS. 1g and 1h) and at the distal femur using micro-computed tomography (μCT) analysis (FIG. 1i-1l).

Example 5: Co-Treatment with miR-19a/b Inhibitors and Intermittent PTH (1-34)

Since both PTH and anti-miR-19a/b increase bone mass, a co-treatment was evaluated. A recombinant fragment of human Parathyroid hormone (PTH 1-34; 100 μg/kg of body weight, Biochem) or vehicle was administered intraperitoneally five times a week for three weeks into 8-week old male mice. Anti-miR-19a/b or scr control was given once a week as co-treatment.

Figure 2:
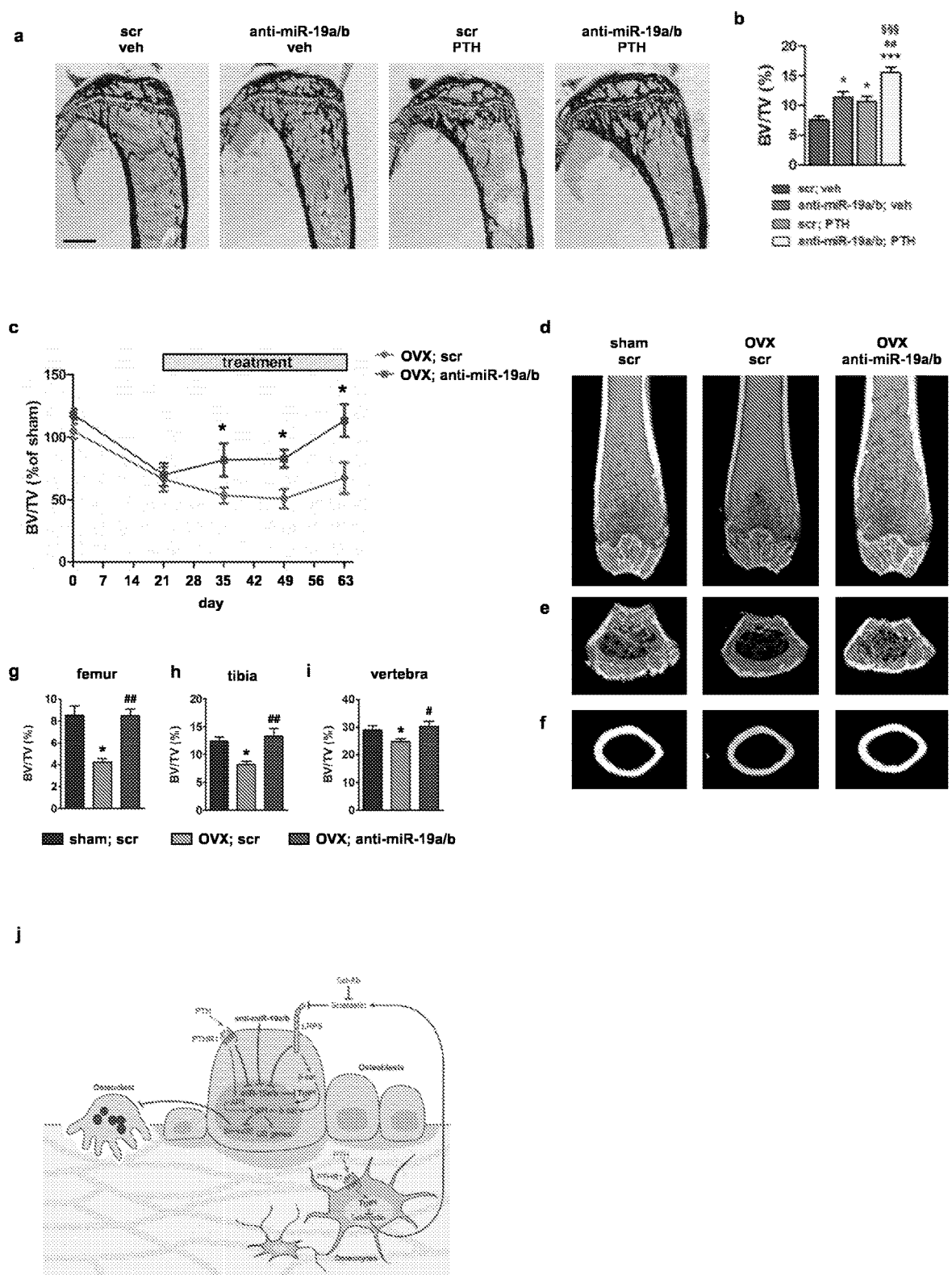
FIG. 2 shows that the inhibition of miR-19a and miR-19b enhances the bone anabolic effect of iPTH treatment and restores bone mass in a mouse model of osteoporosis. (a): Von Kossa staining, and (b): histomorphometric analysis of the proximal tibiae of 12-week old male mice of the genotype Dmp1-Cre−; Tgif1$^{fl/fl}$ after treatment by intermittent PTH and/or weekly injections of anti-miR-19a/b for four weeks. For abbreviations see the legend to FIG. 1. Scale bar indicates 1 mm. (c): Time course of relative BV/TV of the tibiae of female mice in which osteoporosis was induced by ovariectomy (OVX) 21 days before start of weekly treatment with anti-miR-19a/b. (d)-(f), μCT scans of the distal femura (d,e) and of midshaft femoral cross sections (f) of the same animals as in c, after termination of the treatment. (g)-(i), μCT analysis of trabecular BV/TV in femura (g), tibiae (h), and fourth lumbar vertebrae (i) 70 days after ovariectomy. (j) Model of miR-19a/b action. Mean values±SEM. * $p<0.05$, *** $p<0.001$ vs. scr, vehicle; ##$p<0.01$, vs. anti-miR-19a/b, vehicle; §§§ $p<0.001$ vs. scr, iPTH. * $p<0.05$, vs. Sham; scr #$p<0.05$, ##$p<0.01$ vs. OVX; scr.

Results: Anti-miR-19a/b augmented the PTH-mediated increase in bone mass in tibiae of male mice (FIGS. 2a and 2b).

Example 6: miR-19a/b Inhibitors in an Osteoporosis Model

Since a reduced bone mass is the hallmark of osteoporosis, it was tested whether the increase in bone mass by anti-miR-19a/b administration may also be useful for the treatment of female osteoporosis. Hence, 8-week old female mice were ovariectomized to deprive them of their sex steroids which resulted in a severe loss of trabecular bone mass in the tibia. To mimic the clinical situation, anti-miR-19a/b treatment was started after osteoporosis was fully established 21 days after ovariectomy by weekly injections of anti-miR-19a/b or scrambled control.

Results: This therapy prevented further bone loss 14 days after the first treatment, thus alleviating the bone loss in this osteoporosis model. Quantification of the trabecular bone mass of the distal femur, the proximal tibia, and L4 vertebral bodies after termination of the treatment confirmed that anti-miR-19a/b treatment has a protective effect against bone loss in osteoporosis.

Example 7: Histological Analysis of Muscle

The effect of anti-miR-19a/b on ovariectomy-induced loss of muscle function was analyzed. A histological analysis was performed by injected FAM labeled Scrambled or anti-miR-19a/b oligonucleotides once a week (10 mg/kg, i.v.) for 4 weeks into 8-week old C56B1/6 wild-type male mice. One week after the last treatment mice were sacrificed and muscles (M. tibialis anterior) were collected. Muscles were embedded in Optimal Cutting Temperature compound (OCT) prior to frozen sectioning with a cryostat. Tissue sections were stained with Periodic acid-Schiff (PAS) and haematoxylin solutions.

Figure 3:
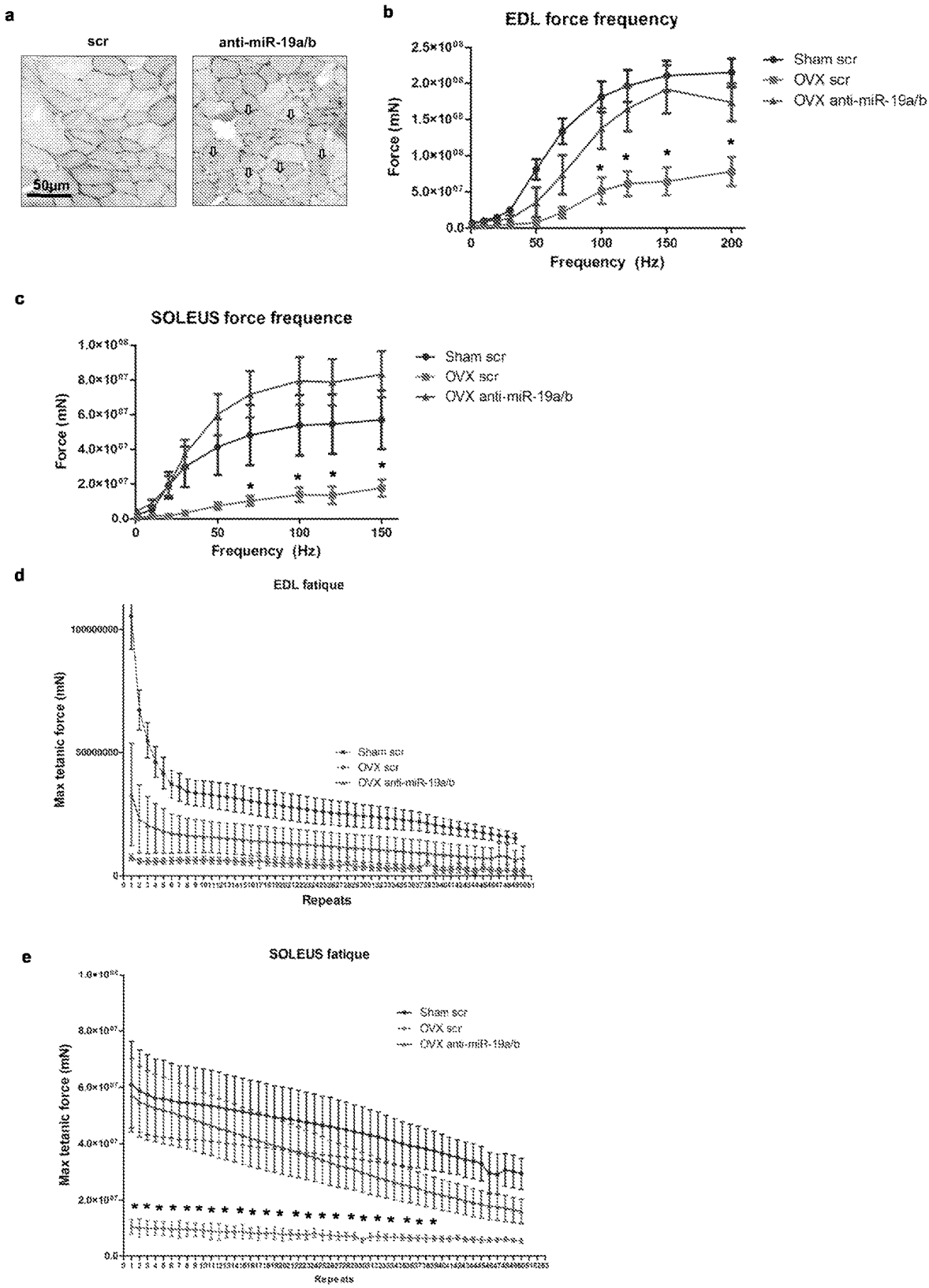
FIG. 3 shows the effect of anti-miR-19a/b on ovariectomy-induced loss of muscle function in mice. (a): histological analysis of M. tibialis anterior from C56B1/6 wild-type male mice that were injected with FAM-labeled scrambled or anti-miR-19a/b oligonucleotides. Arrows indicate central nuclei. (b): ex vivo contractility of M. extensor digitorum longus in ovariectomized or sham operated female C57Bl/6J mice after administration of scrambled (Scr) or anti-miR-19a/b oligonucleotides. (c): ex vivo contractility of M. soleus in ovariectomized or sham operated female C57Bl/6J mice after administration of Scr or anti-miR-19a/b oligonucleotides. (d): ex vivo fatigue of M. extensor digitorum longus in ovariectomized or sham operated female C57Bl/6J mice after administration of Scr or anti-miR-19a/b oligonucleotides. (e): ex vivo fatigue of M. soleus in ovariectomized or sham operated female C57Bl/6J mice after administration of Scr or anti-miR-19a/b oligonucleotides. * $p<0.05$ vs. OVX; scr.
Figure 4:
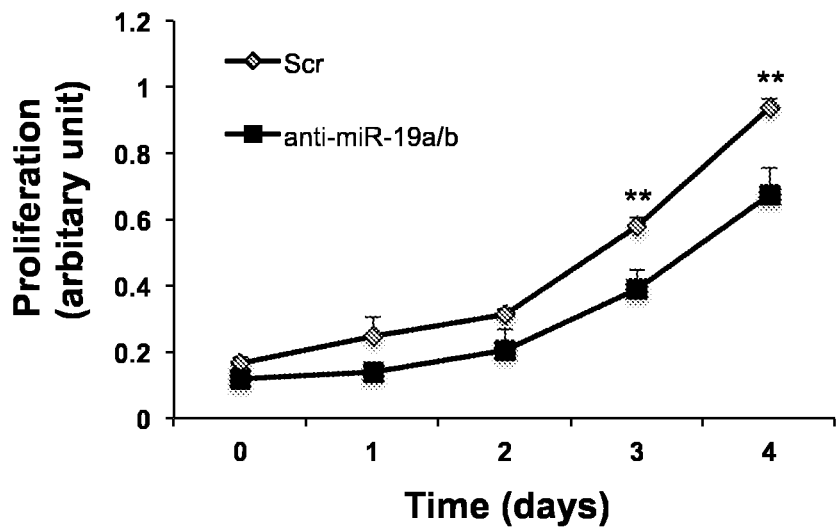
FIG. 4 shows the effect of anti-miR-19a/b on the in vitro growth of bone metastatic MDA-MB-231 breast cancer cells. (a): Proliferation of MDA-MB-231 cells transfected with Scr or anti-miR-19a/b oligonucleotides. (b): Proliferation of MDA-MB-231 cells transfected with Scr or miR-19a/b oligonucleotides. ** $p<0.01$ vs. scr.
Figure 4:
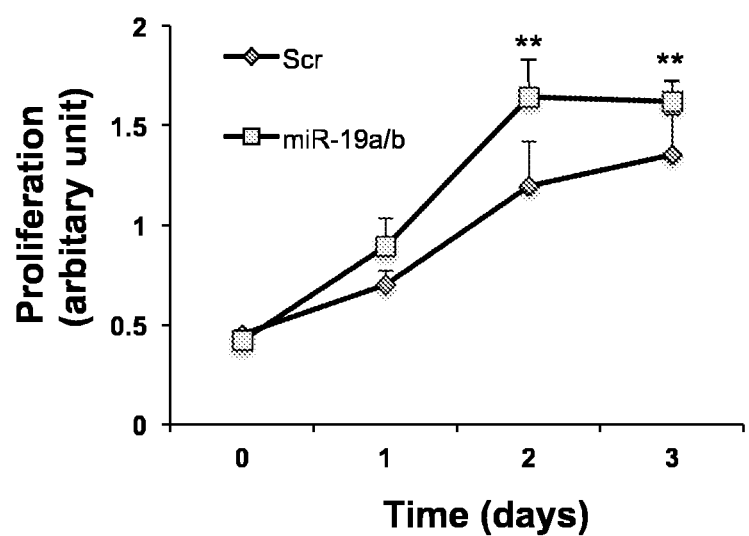

Results: Under steady-state conditions, nuclei are located at the edge of muscle fibers. Interestingly, in anti-miR-19a/b treated myofibers a shift of nuclei from the periphery towards a central position was observed (FIG. 3A), suggesting an active spontaneous muscle tissue remodeling in response to miR-19a/b inhibition.

Example 8: Functional Analysis of Muscle

To investigate the functional implication of the finding reached in Example 7, ex vivo functional tests were performed using freshly harvested muscles (M. extensor digitorum longus and M. soleus). 8-week old female C57Bl/6J mice were ovariectomized or sham operated and treated after three weeks with Scrambled (Scr) or anti-miR-19a/b (10 mg/kg, i.v.) once a week for seven weeks. One week after the last injection mice were sacrificed and ex vivo contractility of the extensor digitorum longus (EDL) and soleus muscle was analyzed using a special device designed for measurement of mouse muscle properties in situ, ex vivo and in vivo (Aurora Scientific). For this purpose, EDL and M. soleus were dissected from the hind limb, steel hooks were tied to the tendons of the muscles and the muscles were mounted between a force transducer. The muscles were stimulated to contract using the supramaximal stimulus between two electrodes. For fatigue studies, M. extensor digitorum longus and M. soleus were stimulated with 70 Hz for 50 repeats and the maximum tetanic force was detected. Data were collected and analyzed using Dynamic Muscle Control/Data acquisition (DMC) and Dynamic Muscle Control Data Analysis (DMA) programs (Aurora Scientific).

Results: The functional tests revealed that ovariectomy significantly decreased strength (FIGS. 3b and 3c) and resilience (FIGS. 3d and 3e) of M. extensor digitorum longus and M. soleus. Anti-miR-19a/b (10 mg/kg, i.v., once a week for seven weeks) restored both strength and resilience to the level of sham control (FIGS. 3b-3e). This strongly suggests that antagonizing miR-19a/b protects against ovariectomy-induced loss of muscle function. These findings indicate that miR-19a/b is a novel target for the treatment of reduced muscle function.

Example 9: Growth of Bone Metastatic Breast Cancer Cells

The above findings support the notion that antagonizing miR-19a/b is osteo-protective. Therefore, it was tested whether anti-miR-19a/b treatment might attenuate the activity of bone destructive MDA-MB-231 breast cancer cells. To test this hypothesis, MDA-MB-231 breast cancer cell were transfected with anti-miR-19a/b, miR-19a/b nucleotides or respective scr controls. Cells were grown 4 days in vitro and cell proliferation was determined by MTS assay each day until the termination of the experiment.

Results: Treatment of bone destructive MDA-MB-231 breast cancer cells with anti-miR-19a/b nucleotides significantly reduced cancer cell proliferation by day 3 and 4, while delivery of miR-19a/b nucleotides increased cancer cell proliferation at the same time points compared to control. These data strongly suggest that inhibition of endogenous miR-19a/b in MDA-MB-231 breast cancer cells might prevent the bone destructive capacity in the context of metastatic breast cancer disease.

Example 10: Treatment of Metastatic Bone Disease

It was tested whether anti-miR-19a/b treatment might attenuate the activity of bone destructive MDA-MB-231 breast cancer cells and protect from breast cancer-induced osteolytic disease in vivo. MDA-MB-231 breast cancer cell stably expressing the luciferase gene were injected into the left ventricle of 8-week old female immunocompromised SCID mice. Micrometastases were detected two weeks after breast cancer cell injection by bioluminescence imaging (BLI), and mice were randomized into two treatment arms. One group received Scrambled oligonucleotide (Scr; 10 mg/kg) and the other group received anti-miR-19a/b (10 mg/kg) intravenously (i.v) once a week for four weeks. Tumor burden was measured weekly by BLI. One week after the last injection, mice were sacrificed and ex vivo contractility of the M. soleus was analyzed using a special device designed for measurement of mouse muscle properties in situ, ex vivo and in vivo (Aurora Scientific). For this purpose, M. soleus was dissected from the hind limb, hooks were tied to the tendons of the muscles, and the muscles were mounted between a force transducer. The muscles were stimulated to contract using the supramaximal stimulus between two electrodes. For fatigue studies, M. soleus was stimulated with 70 Hz for 50 repeats and the maximum tetanic force was detected. Data were collected and analyzed using Dynamic Muscle Control/Data acquisition (DMC) and Dynamic Muscle Control Data Analysis (DMA) programs (Aurora Scientific). Microcomputed tomography ($\mu$CT) was used for three dimensional analyses of long bones. Long bones of mice were analyzed using high-resolution microcomputed tomography with a fixed isotropic voxel size of 10 $\mu$m (70 peak kV at X $\mu$A 400 ms integration time; Viva80 micro-CT; Scanco Medical AG). This threshold was verified by manually evaluating 10 single tomographic slices from four samples per group to isolate the mineralized tissue and to preserve its morphology while excluding nonmineralized tissues. All analyses were performed on the digitally extracted bone tissue using 3D distance techniques (Scanco Medical AG).

Figure 5:
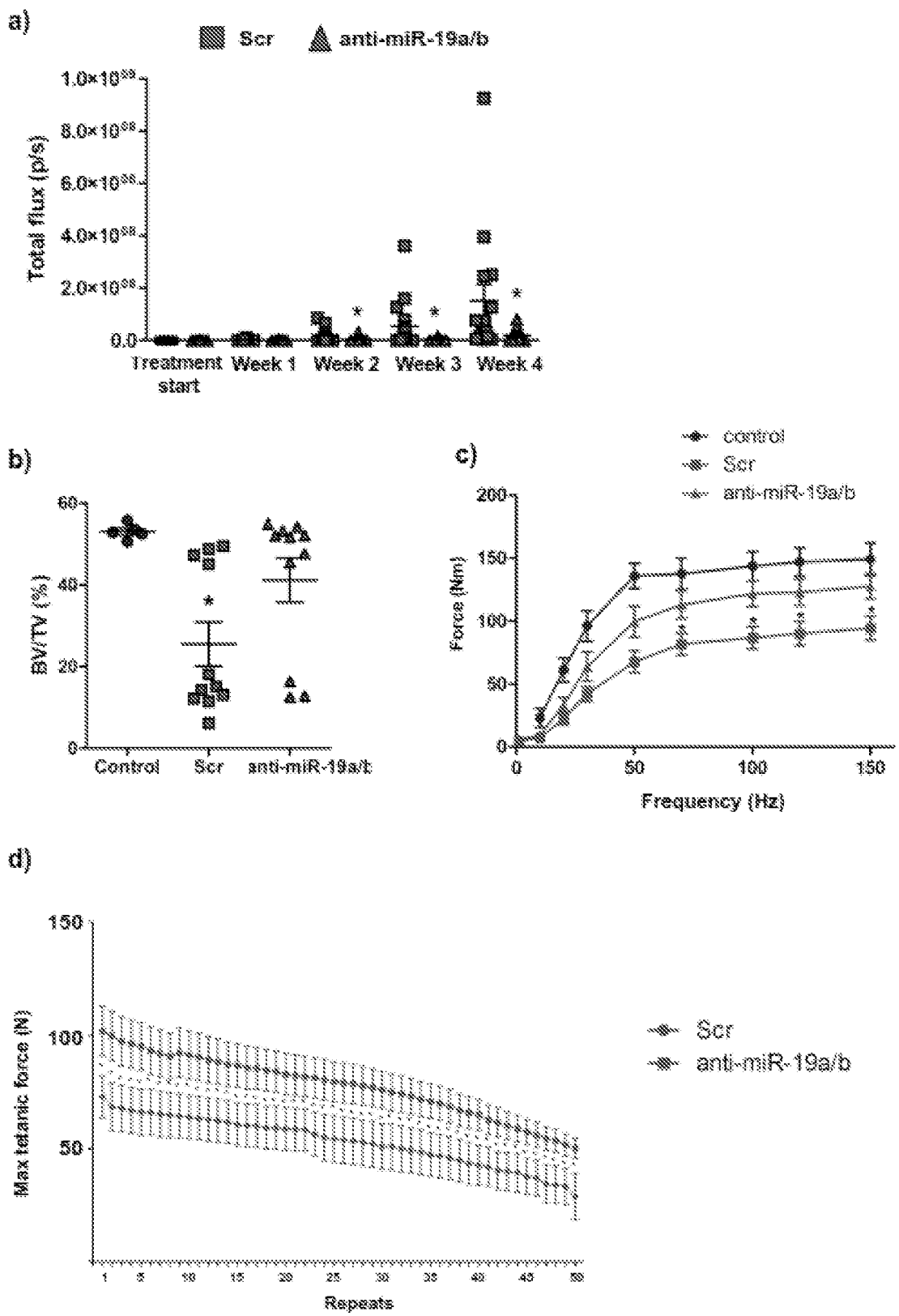
FIG. 5 shows that the inhibition of miR-19a and miR-19b reduces breast cancer bone metastases and restores breast cancer-induced loss of bone mass and muscle function. (a) quantification of bioluminescence signal in tumor bearing mice treated with scrambled (Scr, boxes) or anti-miR-19a/b oligonucleotides (triangles) for four weeks. (b) μCT analysis of the proximal tibiae of non-tumor bearing mice (control) and of mice with bone metastases after treatment with Scr or anti-miR-19a/b oligonucleotides. (c) ex vivo contractility of M. soleus in non-tumor bearing mice (control) and in tumor bearing mice after administration of Scr or anti-miR-19a/b oligonucleotides. (d) ex vivo fatigue of M. soleus in non-tumor bearing mice (control) and in tumor bearing mice administrated with Scr or anti-miR-19a/b oligonucleotides. Mean values±SEM. * $p<0.05$ vs. non-tumor bearing mice.

Results: BLI imaging revealed a significantly reduced tumor growth in the bones of anti-miR-19a/b treated mice compared to Scr treated controls (FIG. 5a). Breast cancer induced significant bone loss in mice treated with Scr which was prevented by weekly anti-miR-19a/b treatment (FIG. 5b). The functional muscle tests revealed that anti-miR-19a/b (10 mg/kg, i.v., once a week for four weeks) restored cancer-induced loss of both strength and endurance of M. soleus (FIGS. 5c and 5d). This strongly suggests that antagonizing miR-19a/b reduces bone metastatic burden and protects against breast cancer-induced loss of bone mass and muscle function.

Example 11: Treatment of Glucocorticoid-Induced Osteoporosis

To investigate whether anti-miR-19a/b is implicated in glucocorticoid-induced osteoporosis, placebo or prednisolone (2.1 mg/kg/d) pellets were subcutaneously implanted in 4-month old female C57Bl/6J mice. One day prior pellet implantation and subsequently once a week mice were treated with Scrambled (Scr) or anti-miR-19a/b (10 mg/kg, i.v.). Bone mineral density (BMD) and body fat mass were measured before and after 4 weeks of treatment using dual-energy x-ray absorptiometry (DEXA, Piximus). In vivo muscle force was determined after 2 weeks of treatment using a vertical forelimb grip strength test. In vivo functional muscle tests (plantarflexion torque) were performed using the special device designed for measurement of mouse muscle properties in vivo (Aurora Scientific). Maximum muscle contraction force was normalized to body weight. After 4 weeks of treatment, mice were sacrificed and the wet weight of gastrocnemius, quadriceps and Tibialis Anterior (TA) muscles was measured.

Figure 6:
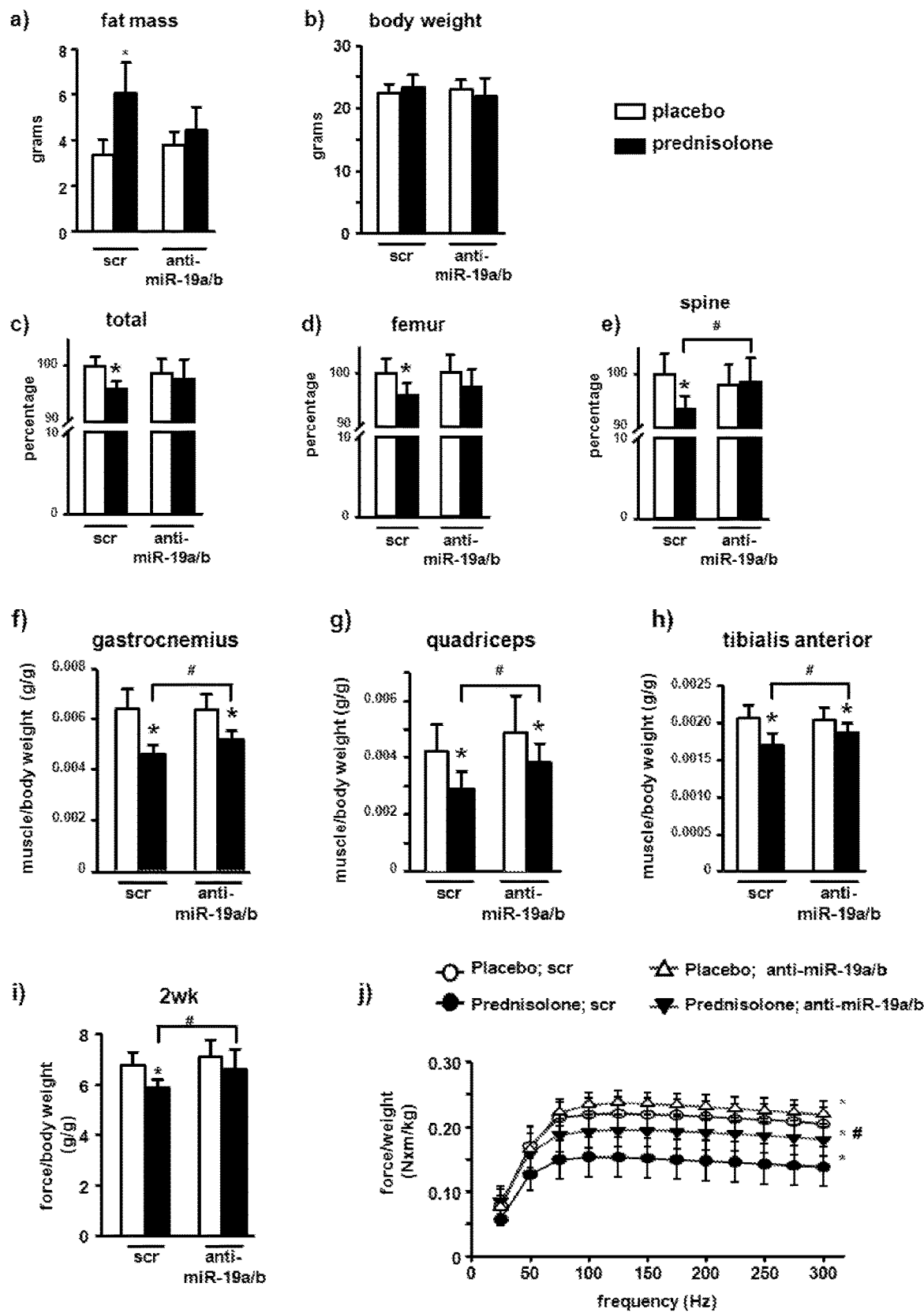
FIG. 6 shows the effect of anti-miR-19a/b on glucocorticoid-induced loss of bone mass and muscle function in mice. (a) Fat mass in mice upon placebo or glucocorticoid (prednisolone) treatment, and delivery of scrambled (Scr) or anti-miR-19a/b oligonucleotides measured by Dual-energy x-ray absorptiometry (DXA). (b) Body weight measured by DXA. (c)-(e) DXA analysis of bone mineral density in mice upon placebo or prednisolone treatment, and delivery of Scr or anti-miR-19a/b oligonucleotides in total body (c), femura (d) and spine (e). (f)-(h) Muscle wet weight of gastrocnemius (f), quadriceps (g) and tibialis anterior (h) in mice treated with placebo or prednisolone and Scr or anti-miR-19a/b oligonucleotides. (i) In vivo muscle force determined after 2 weeks of treatment with placebo or prednisolone and Scr or anti-miR-19a/b oligonucleotides using a vertical forelimb grip strength test. (j) In vivo functional muscle test (plantarflexion torque) in mice treated with placebo or prednisolone and Scr or anti-miR-19a/b oligonucleotides. Mean values±SEM. * $P<0.05$ vs. corresponding placebo treated mice, #$P<0.05$ vs. prednisolone and scr treated mice.

Results: Dual-energy x-ray absorptiometry measurement revealed an increased fat mass upon glucocorticoid (prednisolone) treatment, which was prevented by weekly delivery of anti-miR-19a/b (FIG. 6a). No change was observed in total body weight (FIG. 6b). Furthermore, BMD was significantly reduced in the femura and in the spine of mice receiving prednisolone (FIG. 6c-e). Mice treated with anti-miR-19a/b were protected from the glucocorticoid-induced loss of BMD (FIG. 6c-e). Although glucocorticoids reduced muscle mass in both Scr and anti-miR-19a/b treated mice, gastrocnemius, quadriceps and tibialis anterior muscle mass of was significantly higher in anti-miR-19a/b treated mice compared to Scr treated controls (FIG. 6f-h). Importantly, anti-miR-19a/b treatment prevented glucocorticoid-induced loss of muscle function determined by grip force and plantarflexion torque tests (FIG. 6i, j).

LITERATURE

1. Janssen, H. L. A. et al., Treatment of HCV Infection by Targeting MicroRNA, N. Engl. J. Med. 368, 1685-1694 (2013).
2. Musilova K. & Mraz M., MicroRNAs in B cell lymphomas: How a complex biology gets more complex", Leukemia, 2015 29 (5), 1004-17 (2015).
3. Nielsen B. S., et al., High levels of microRNA-21 in the stroma of colorectal cancers predict short disease-free survival in stage II colon cancer patients, Clin Exp Metastasis 28 (1): 27-38 (2010).
4. Romao J. M. et al., MicroRNA regulation in mammalian adipogenesis, Exp. Biol. Med. 236 (9), 997-1004 (2011).
5. Hommers L. G. et al., Heterogeneity and Individuality: microRNAs in Mental Disorders, J Neural Transm. 122 (1): 79-97 (2015).
6. Parfitt, A. M. et al., Bone histomorphometry: standardization of nomenclature, symbols, and units. Report of the ASBMR Histomorphometry Nomenclature Committee. J. Bone Miner. Res. 2, 595-610 (1987).

---

The invention claimed is:

1. A method of treating or preventing osteogenesis imperfecta (OI), cancer-related bone destruction caused by bone metastasis, muscle atrophy, cachexia or sarcopenia, said method comprising administering an inhibitor of microRNA 19a and/or microRNA 19b to a subject in need thereof, wherein said inhibitor is a nucleic acid or nucleic acid analog.

2. The method of claim 1, wherein said method also includes the administration of parathyroid hormone or a fragment thereof.

3. The method of claim 1, wherein said inhibitor comprises a DNA or RNA sequence that binds to or reduces the expression of microRNA 19a and/or microRNA 19b.

4. The method of claim 1, wherein said inhibitor is administered by intravenous, subcutaneous, transdermal, or transmucosal administration.

5. The method of claim 1, wherein said inhibitor is administered by infusion or injection.

6. The method of claim 1, comprising administering a pharmaceutical composition comprising said inhibitor of microRNA 19a and/or microRNA 19b and a pharmaceutically acceptable carrier to said subject.

7. The method of claim 1, wherein said inhibitor is a DNA comprising:
   (a) the sequence of SEQ ID NO:1 or SEQ ID NO:2, or
   (b) the complement of the sequence of SEQ ID NO:1 or SEQ ID NO:2, or
   (c) a variant of any of the sequences of (a) or (b) which has at least 70% sequence identity thereto and is capable of hybridizing to microRNA 19a and/or microRNA 19b.

* * * * *